(12) United States Patent
Boursier Niutta

(10) Patent No.: US 10,722,142 B2
(45) Date of Patent: Jul. 28, 2020

(54) MEDICAL APPARATUS FOR THE INTRODUCTION OF CATHETERS INTO THE HUMAN BODY

(71) Applicant: Enrico De Lutio, Amelia (IT)

(72) Inventor: Stefano Boursier Niutta, Naples (IT)

(73) Assignee: PILOT TECHNOLOGIES S.R.L, Rome (IT)

( * ) Notice: Subject to any disclaimer, the term of this patent is extended or adjusted under 35 U.S.C. 154(b) by 96 days.

(21) Appl. No.: 15/978,471

(22) Filed: May 14, 2018

(65) Prior Publication Data

US 2018/0256068 A1     Sep. 13, 2018

Related U.S. Application Data

(63) Continuation-in-part of application No. PCT/IB2017/055491, filed on Sep. 12, 2017.

(30) Foreign Application Priority Data

Sep. 12, 2016  (IT) .................. 102016000091852

(51) Int. Cl.
*A61B 5/04* (2006.01)
*A61B 5/06* (2006.01)
(Continued)

(52) U.S. Cl.
CPC ............ *A61B 5/065* (2013.01); *A61B 5/0452* (2013.01); *A61B 5/04085* (2013.01);
(Continued)

(58) Field of Classification Search
None
See application file for complete search history.

(56) References Cited

U.S. PATENT DOCUMENTS 7,794,407 B2  9/2010  Rothenberg
8,155,732 B2  4/2012  Scholz et al.
(Continued)

FOREIGN PATENT DOCUMENTS

WO   WO2008/129326 A1   10/2008
WO   WO2009/100158 A1   8/2009
(Continued)

OTHER PUBLICATIONS

Cavanna L. et al., "Studio clinico osservazionale per la valutazione della posizione della punta dell'accesso venoso centrale ad inserzione brachiale tramite la tecnica dell 'ECG intracavitario" Oct. 10, 2015 (with computer translation).
(Continued)

*Primary Examiner* — Ankit D Tejani
(74) *Attorney, Agent, or Firm* — Davidson, Davidson & Kappel, LLC

(57) ABSTRACT

A medical apparatus for the introduction of catheters into the human body including: an ECG device having at least three electrodes, positionable on a human body for the detection of surface electrical potential data and adapted to provide at output at least one surface ECG strip; at least one catheter element having a distal ending part positionable inside the human body and having an auxiliary electrode element for the detection of intracavitary electrical potential data, associated with the ECG device for sending to the latter said intracavitary data, the ECG device being adapted to provide at output at least one intracavitary ECG strip; —an electronic device associated with the ECG device for the receipt of at least said intracavitary ECG strip and comprising a data processing module (10) adapted to process at least the intracavitary ECG strip to obtain usage information adapted at least to provide instructions on the insertion of the catheter element in the human body.

11 Claims, 6 Drawing Sheets

(51) Int. Cl.
    *A61B 8/12*     (2006.01)
    *A61B 5/0452*     (2006.01)
    *A61B 5/053*     (2006.01)
    *A61B 5/00*     (2006.01)
    *A61B 5/0408*     (2006.01)
    *A61B 5/0215*     (2006.01)

(52) U.S. Cl.
    CPC ............ *A61B 5/0538* (2013.01); *A61B 5/061* (2013.01); *A61B 5/6852* (2013.01); *A61B 8/12* (2013.01); *A61B 5/0215* (2013.01)

(56) References Cited

U.S. PATENT DOCUMENTS

| | | |
|---|---|---|
| 8,781,555 B2 | 7/2014 | Burnside et al. |
| 8,801,693 B2 | 8/2014 | He et al. |
| 9,125,578 B2 | 9/2015 | Grunwald |
| 9,265,443 B2 | 2/2016 | Rothenberg |
| 9,445,734 B2 | 9/2016 | Grunwald |
| 9,445,746 B1 | 9/2016 | Elberse et al. |
| 9,839,372 B2 | 12/2017 | Bukhman et al. |
| 9,854,992 B2 | 1/2018 | Grunwald et al. |
| 10,206,622 B2 | 2/2019 | Narusawa et al. |
| 10,231,643 B2 | 3/2019 | Grunwald |
| 10,321,846 B2 | 6/2019 | Grunwald et al. |
| 2012/0059270 A1 | 3/2012 | Grunwald |
| 2013/0018248 A1 | 1/2013 | Hurezan |
| 2015/0216446 A1 | 8/2015 | Bukhman et al. |
| 2015/0282734 A1 | 10/2015 | Schweikert et al. |
| 2015/0317810 A1 | 11/2015 | Grunwald et al. |
| 2016/0278869 A1 | 9/2016 | Grunwald |

FOREIGN PATENT DOCUMENTS

| | | |
|---|---|---|
| WO | WO2009/129477 A1 | 10/2009 |
| WO | WO2009/129484 A1 | 10/2009 |
| WO | WO2010/144922 A1 | 12/2010 |
| WO | WO2011/116896 A1 | 9/2011 |
| WO | WO2012/068365 A1 | 5/2012 |
| WO | WO2012/040487 A1 | 3/2014 |
| WO | WO2014/137841 A1 | 9/2014 |
| WO | WO2017/122117 A1 | 7/2017 |

OTHER PUBLICATIONS

Moureau et al., "Electrocardiogram (EKG) Guided Peripherally Inserted Central Catheter Placement and Tip Position: Results of a Trial to Replace Radiological Confirmation", Association for Vascular Access. vol. 15. No. 1, 2010, pp. 8-14.

McGee et al., "Accurate Placement of Central Venous Catheters: A Prospective, Randomize, Multicenter Trail." Critical Care Medicine, vol. 21 No. 8, Aug. 1993, p. 1118-1123.

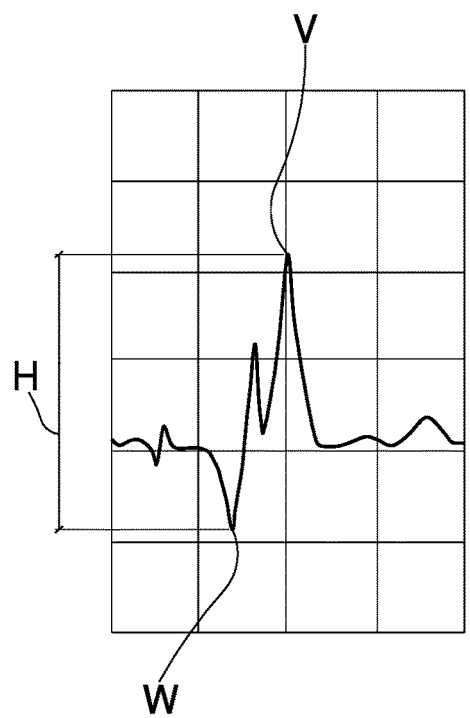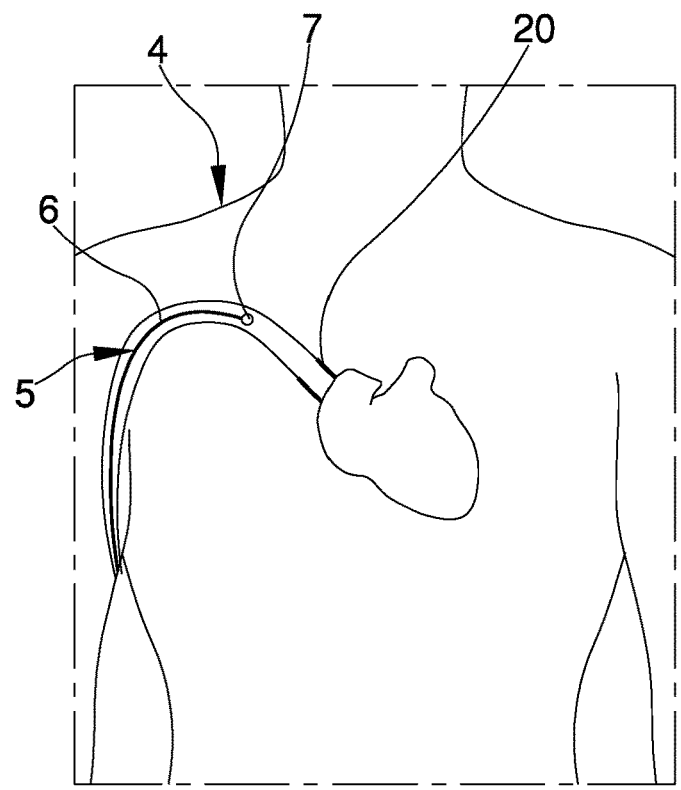
Fig.8
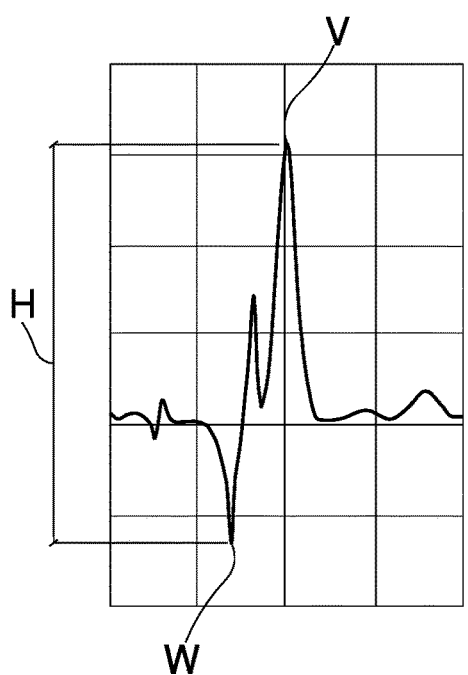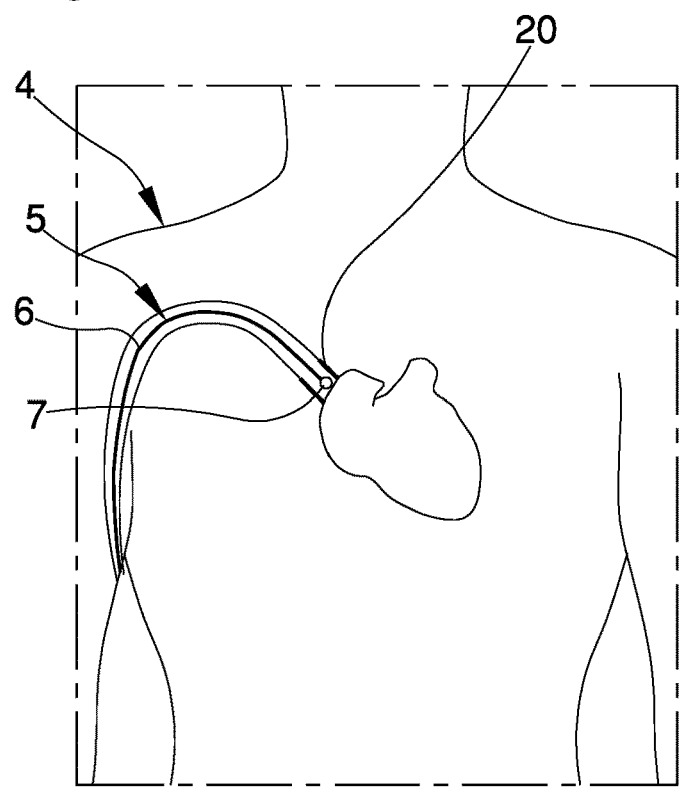
Fig.9

MEDICAL APPARATUS FOR THE INTRODUCTION OF CATHETERS INTO THE HUMAN BODY

This is a Continuation-in-Part of International Patent Application PCT/IB2017/055491, filed Sep. 12, 2017 claiming priority to Italian Patent Application IT102016000091852, filed Sep. 12, 2016, both of which are hereby incorporated by reference herein.

The present invention relates to a medical apparatus for the introduction of catheters into the human body for the processing of electrocardiographic data.

BACKGROUND

In the medical field, the use is known of special devices to detect the electrical activity behind heart function, both for diagnostic purposes and for simple purposes of heart activity monitoring.

Generally, such devices are provided with at least three electrodes to be positioned on the patient's body in order to detect the differences in potential which are created during cardiac activity.

The electrodes are positioned to form a triangle (Einthoven triangle) and are operatively linked to processing means adapted to graphically plot the pattern of the signal relating to the electrical activity of the heart over time.

The resulting pattern is known as electrocardiogram (ECG) and provides useful information on the patient's health condition, particularly related to health conditions tied to heart activity.

For each detection operation, three different ECG strips are obtained, these being the projection of the resulting cardiac activity on the three directions identified by the sides of the Einthoven triangle.

In particular, reference is made to the first derivation for the ECG strip relating to the right shoulder-left shoulder direction; to the second derivation for the ECG strip relating to the left inguinal-right shoulder direction; to the third derivation for the ECG strip relating to the left inguinal-left shoulder direction. By way of example, an ECG strip, referring to a cardiac cycle of a patient not subject to fibrillation, in first and second derivation, has the following major points:

wave P: this is the first section of the ECG which has a relative maximum point, conventionally positive with respect to the line, unlike zero potential difference defined as "isoelectric", and refers to the wave and originates in the sino-atrial node and points to the depolarization of the atria;

group QRS: this is a complex of three successive waves reflecting the progressive depolarization of the ventricles, with the depolarization wave passing from the atrium-ventricular node to the surface of the ventricles.

The Q wave is negative with respect to the isoelectric and corresponds to the depolarization of the interventricular septum; the wave R is positive and has the maximum adjustable peak and corresponds to the depolarization of the left ventricle apex; the wave S is negative and corresponds to the depolarization of the part of the ventricles in contact with the atria;

wave T: this has a positive relative maximum and corresponds to the phase of re-polarization of the ventricle cells.

In third derivation, the ECG strip shows differences in representation due to the variability of the vector representing electrical activity, with the wave T, for example, which is negative.

In any case, a distinction can be made between the same major points.

From an examination of the ECG strips, the medical staff is able to obtain information on the patient's health, or to obtain useful information of various types.

The use is in fact known of the devices described above, for the sake of simplicity called ECG devices, as support instruments in the implanting of central venous catheters (CVC), of totally implantable systems and of catheters for hemodialysis.

The CVC implant in fact envisages the insertion of the catheter into a blood vessel making it run along this until the ending part of the catheter itself is positioned at the cavoatrial junction.

The most commonly used technique, to date, envisages the use of an ECG device connected to the ending part of the catheter, the latter used as an electrode to detect the differences in potential, so as to "guide" the doctor in the positioning of the ending part itself.

As the ending part of the catheter is pushed towards the cavoatrial junction, the ECG strip undergoes changes due to the change in position of the electrode with respect to the catheter.

According to established practice, doctors make reference to changes in the height of the wave P, considering as point of arrival the positioning whereby the ECG strip shows the maximum value of such height.

In detail, the doctor inserts the catheter and pushes it with gradual and predefined forward movements towards the cavoatrial junction, observing the ECG strip for each forward movement.

On the basis of his/her experience, the doctor checks the pattern of the wave P and establishes the final position of the catheter.

Usually, when the wave P starts to decrease, or even shows an initial negative section, the doctor returns to the immediately preceding position, considering him/herself to be close to the cavoatrial junction.

This known technique has a number of drawbacks tied to the fact that most of the work is entrusted to the doctor's experience.

The chosen final position may not be the ideal one, inasmuch as many factors accidentally influence the correct detection of the electrical activity of the heart. In order to address this type of drawback, proceeding is known with the aid of a radiographic control adapted to detect the position of the ending part of the catheter by X rays.

This solution too has a number of drawbacks tied to exposure to the X rays, known to be harmful for human health, and to the difficulty in controlling the position when the ending part of the catheter is covered by bone parts.

SUMMARY OF THE INVENTION

It is an object of the present invention to provide a medical apparatus for the introduction of catheters into the human body which allows improving catheter implants.

One object of the present invention is to provide a medical apparatus for the introduction of catheters into the human body which allows an effective support for central venous catheter implants.

Another object of the present invention is to provide a medical apparatus for the introduction of catheters into the human body which permits improving the health and safety conditions of the patients undergoing central venous catheter implants.

Another object of the present invention is to provide a medical apparatus for the introduction of catheters into the human body which allows providing information on the operating conditions of the central venous catheters already implanted.

Another object of the present invention is to provide a medical apparatus for the introduction of catheters into the human body which allows to overcome the aforementioned drawbacks of the prior art within the ambit of a simple, rational, easy, efficient to use and cost-effective solution.

The aforementioned objects are achieved by the present medical apparatus for the introduction of catheters into the human.

The invention may comprise one or more of the following features:

said electronic device comprises at least one memory unit associated at least with said data processing system;

it comprises an ultrasound scanning device associated with said electronic device to obtain ultrasound scanned images.

it comprises a user interface module, associated with said electronic device.

BRIEF DESCRIPTION OF THE DRAWINGS

Other characteristics and advantages of the present invention will become more evident from the description of a preferred, but not exclusive, embodiment of a medical apparatus for the introduction of catheters into the human body, illustrated by way of an indicative, but non-limiting example, in the attached drawings in which:

FIGS. 8 and 9 are schematic illustrations of the operation of a second embodiment of the apparatus according to an embodiment of the invention.

DETAILED DESCRIPTION

Figure 1:
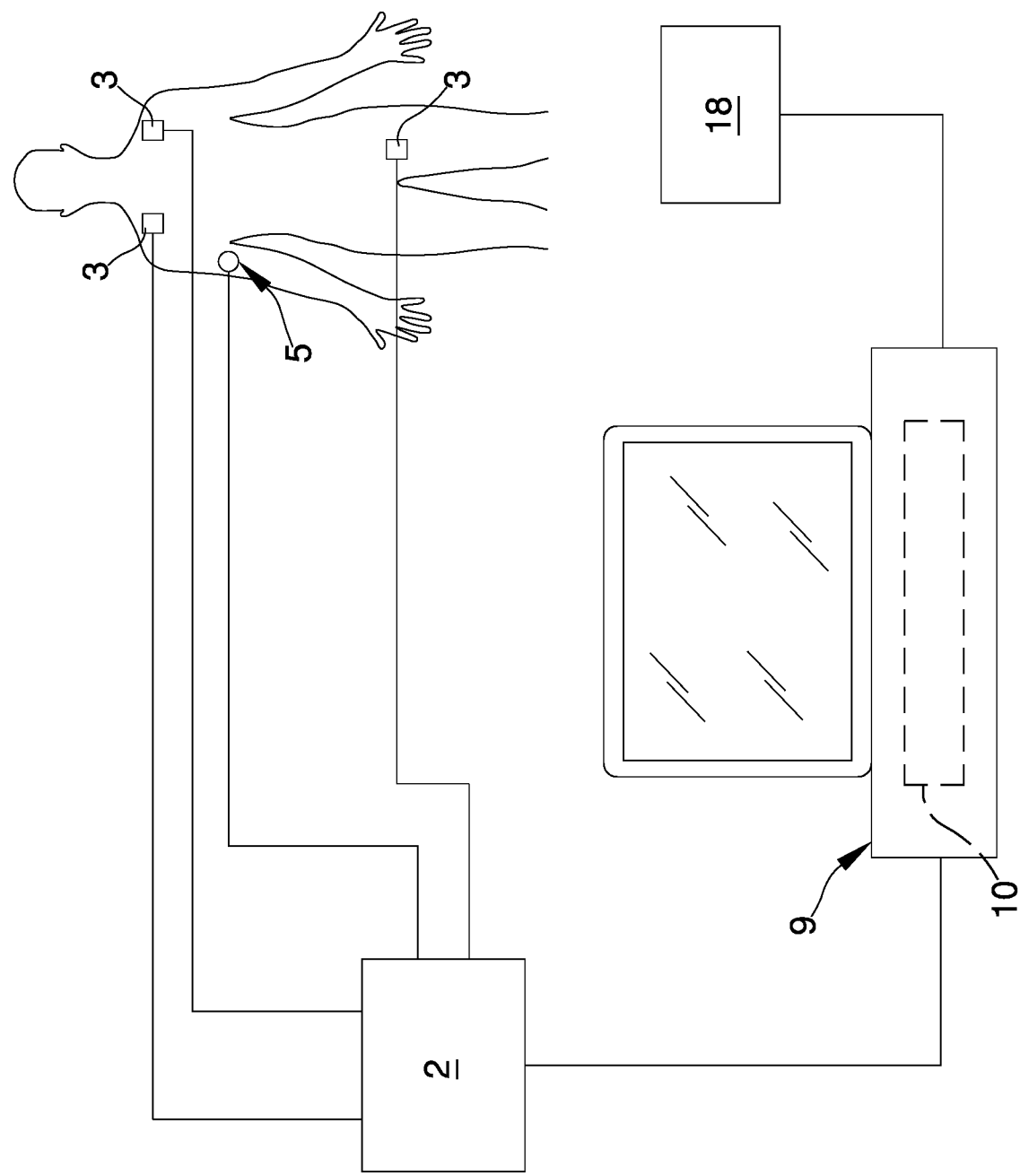
FIG. 1 is a schematic general view of the medical apparatus according to an embodiment of the invention.

With particular reference to these illustrations, reference numeral 1 globally indicates a medical apparatus for the introduction of catheters into the human body.

According to an embodiment of the invention, the apparatus 1 comprises an electrocardiogram device, for sake of simplicity indicated in the present treatise by the term ECG device and by reference numeral 2.

The ECG device 2 has at least three electrodes 3, positionable on a human body 4 for the detection of surface electrical potential data that is electrical potential data which can be detected at the body surface.

Consistently with what has been written above, the ECG device 2 is adapted to provide at output a surface ECG strip in the form of a signal, for simplicity not illustrated in the figures, i.e. referred of potential differences detected on the body surface, which represent the module of a vector the direction and orientation of which are determined by the position of the electrodes.

The apparatus 1 also comprises at least one catheter element 5, schematically illustrated in the figures as a hollow tubular element.

The catheter element 5 has a distal ending part 6, illustrated in a simplified manner in the figures, positionable inside the human body 4.

The distal ending part 6 has an auxiliary electrode element 7 for the detection of intracavitary electrical potential data, i.e. referred to electrical potential data detectable within a cavity of the human body, particularly within a vein.

In this case, the auxiliary electrode element 7 is the catheter itself that, filled with water, acts as a water column.

The catheter element 5 is associated with the ECG device 2 for sending intracavitary data to the latter, with the ECG device which is adapted to provide at output at least one intracavitary ECG strip 8 in the form of a processable signal.

Such characteristic allows using the same ECG device 2 to obtain both surface ECG strips, and intracavitary ECG strips.

The surface ECG strips are obtained from data provided by the electrode elements 3, while the intracavitary ECG strips are obtained from the data provided by the auxiliary electrode 7 combined with the data provided by two other electrode elements 3.

In the present embodiments, the surface ECG strips and the intracavitary ECG strips refer to the "second derivation", but the same considerations can also be made for first and third derivation strips.

Advantageously, the apparatus comprises an electronic device 9 associated with the ECG device 2 to receive the intracavitary ECG strip 8 and the ECG strip. In particular, the electronic device 9 comprises a data processing module 10 adapted to process the intracavitary ECG strip 8, and possibly the other ECG strips, for obtaining usage information H.

Usage information H is adapted to provide instructions on the insertion of the catheter element 5 into the human body 4 and, along with all other information, data and parameters coming from the electronic device 9, is useful to medical staff during the insertion operations of the catheter element 5 into the human body 4.

In the present treatise, reference is made to a "medical operator" but other figures cannot be ruled out belonging to the medical staff.

For example, besides the data directly detectable by the ECG device, such as heart rate, usage information will be the data coming from the ECG strip printouts.

In particular, the usage information H is at least in part of the type of heights measured on the ECG strip.

Conveniently, the module 10 comprises first processing means 11 associated with the ECG device 2 for the acquisition of at least the intracavitary ECG strip 8 so as to obtain recognition data Q, R, S, P, T, V, W, J which are adapted to provide analytical information on the ECG strip 8.

The recognition data Q, R, S, P, T, V, W, J are data deriving from an analysis of the signal of the intracavitary ECG strip 8 and permit locating particular values on the strip itself such as the relative maximums and minimums, or constant-height points.

To this purpose, the first processing means 11 comprise a first data processing unit 12 receiving at input the intracavitary ECG strip 8 to obtain first recognition data Q, R, S, P, T, V, W of maximum and minimum points referred to the same strip.

In the first data processing unit 12, the intracavitary ECG strip 8 is analyzed and the relative maximum and minimum points are recognized referred to a heart cycle and are indicated by the reference letters P, Q, R, S, T, V and W.

P, Q, R, S, T correspond to the maximum and minimum values of a typical ECG strip, while V and W correspond to the absolute maximum and absolute minimum values of the ECG strip analyzed in a heart cycle.

The first processing means 11 also comprise a second data processing unit 13 receiving at input the intracavitary ECG strip 8 and the first recognition data Q, R, S, P, T, V, W to obtain second recognition data J of points of an isoelectric line of the same strip.

In the second data processing unit 13, the signal of the intracavitary ECG strip 8 is analyzed, preferably, but not exclusively, in combination with the first recognition data Q, R, S, P, T, V, W and the isoelectric line is identified of the strip itself, i.e., the line whose points have a substantially identical electric potential value.

The difference in potential in these points of the ECG strip is not very appreciable, and consequently such points are substantially aligned along a straight line, conventionally called isoelectric line and indicated by the reference letter K.

The present embodiments require the first processing means 11 to be able to also acquire the surface ECG strip, and the signal printouts described for the intracavitary ECG strip 8 can be made in the same way for the surface strip as well.

Advantageously, the module 10 comprises second processing means 14 associated at least with the first processing means 11 for the acquisition and processing of at least the recognition data Q, R, S, P, T, V, W, J to obtain the usage information H.

The second processing means 14, therefore, acquire the information on points P, Q, R, S, T, V, W and on the isoelectric line K, and process them to obtain information useful to the medical operator, e.g., information related to the change in height values for intracavitary ECG strips 8 found for different positions of the distal ending part 6.

Conveniently, the electronic device 9 comprises at least one memory unit 15 associated at least with the module 10.

Figure 2:
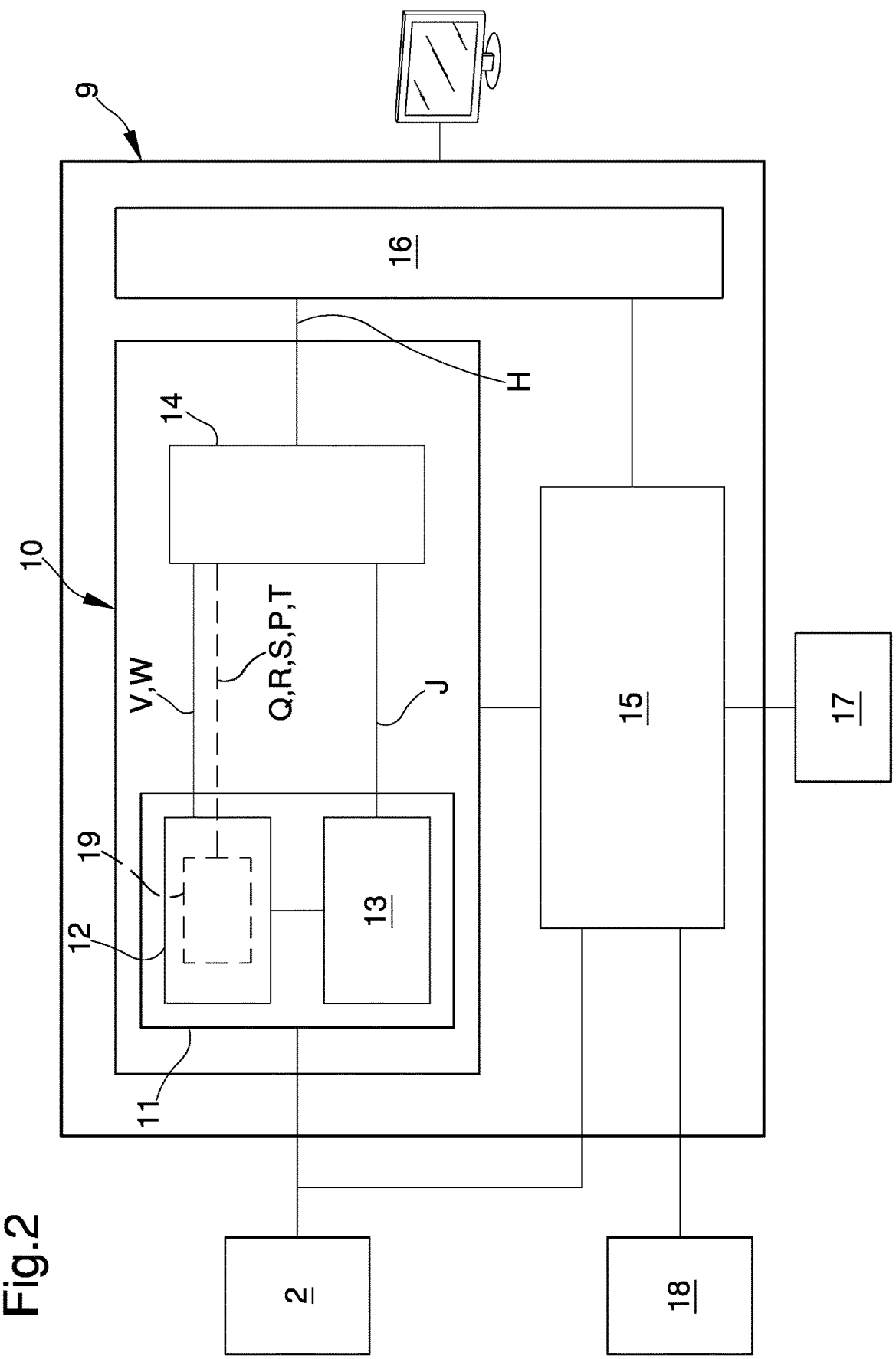
FIG. 2 is a schematic view of a detail of a first embodiment of the medical apparatus according to an embodiment of the invention.
Figure 3:
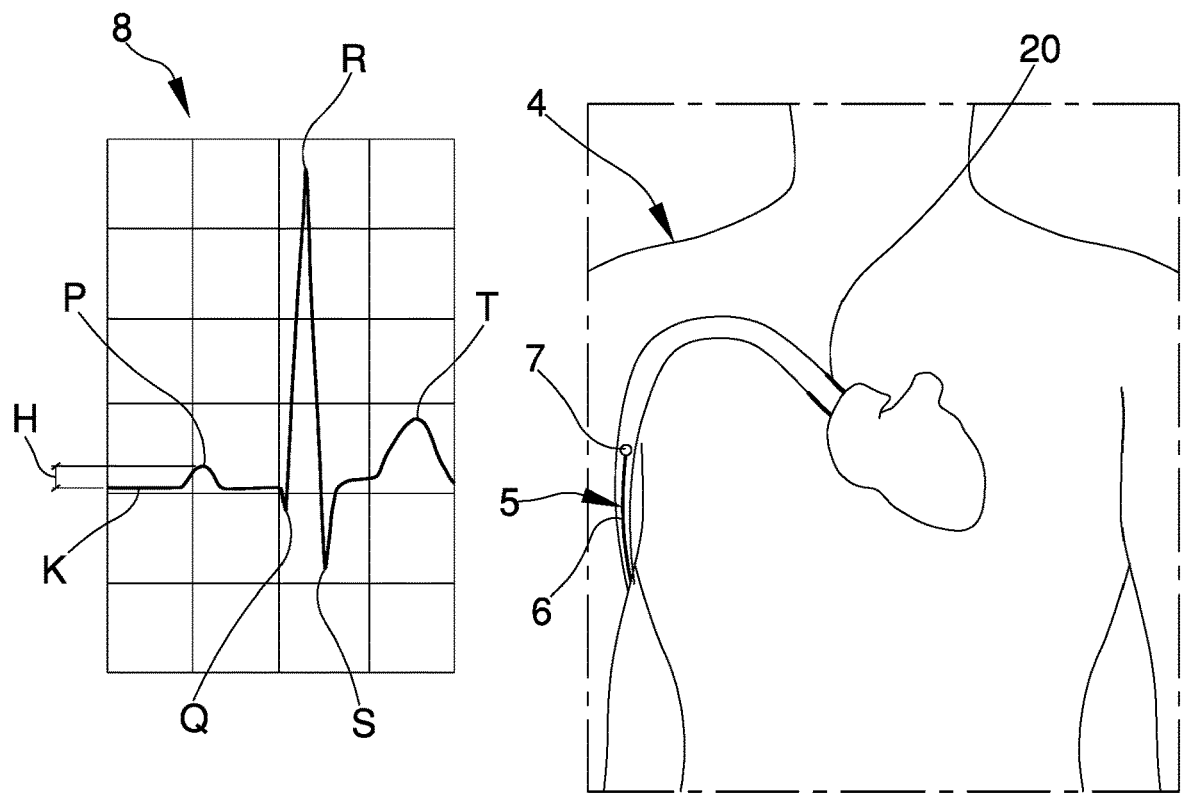
FIGS. 3 to 6 are schematic illustrations of the operation of a first embodiment of the apparatus according to an embodiment of the invention.
Figure 4:
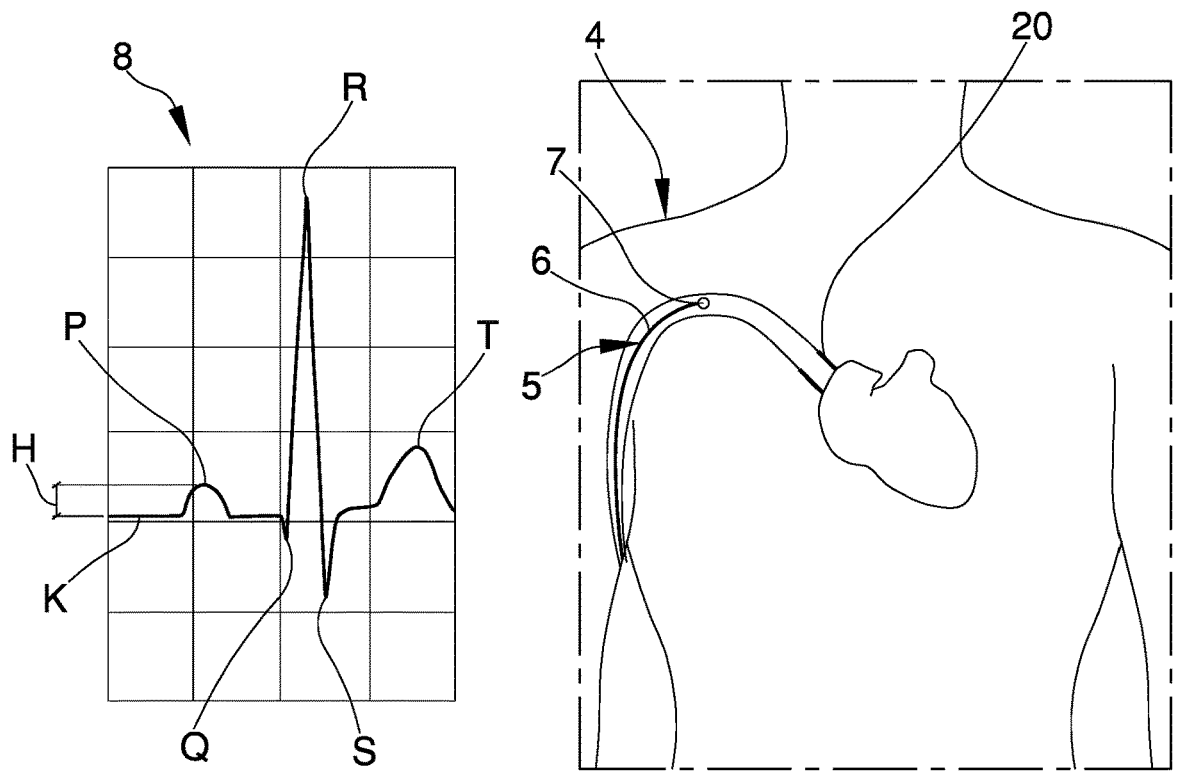

As shown in FIG. 2, the memory unit is connected to both the ECG device 2, and to the module 10 so as to allow storage of the ECG strips and of the data which are processed inside the module itself.

This way, therefore, the processed data and the usage information H can be recorded in order to obtain a historic record of the ECG strips and of the data related to them.

Conveniently, the electronic device 9 comprises at least one output unit 16 associated at least with the module 10 and adapted to provide at output usage information H or other data, such as the ECG strips, the data processed in the module 10 and other information stored in the memory unit 15.

As schematically shown in the illustrations, the output unit 16 is connectable to a screen so as to permit displaying the information H and the other data.

Such feature allows the medical operator to display all the information useful for inserting the catheter element 5 into the human body 4 of the patient on a simple monitor.

The output unit 16, furthermore, comprises connection means, not shown for the sake of simplicity, which allow transmitting the data and the information from the electronic device 9 to any one other destination unit such as, e.g., external peripheral units (USB pen drive, hard-disk and other similar solutions), networks for transmitting data via cable, transceiver devices for transmitting data through electromagnetic waves (wi-fi, bluetooth, radio).

The apparatus also comprises a user interface module 17, associated with the electronic device 9.

The user interface module 17 enables the medical operator, any other operator, to enter data and information directly in the electronic device 9, or to manage the processed data and information according to need.

Advantageously, the apparatus 1 comprises an ultrasound scanning device 18 associated with the electronic device 9 to obtain ultrasound scanned images. Usefully, the ultrasound device 18 is associated with the memory unit 15 to record and transmit ultrasound images.

This way, besides the information and data processed in the module 10, the operator can display, live or subsequently, ultrasound images showing the vein and the catheter element 5.

In a first embodiment, the first processing means 11 comprise an additional unit 19 for processing the first recognition data Q, R, S, P, T, V, W to obtain first input data Q, R, S and second input data P.

In particular, the first additional unit 19 processes the recognition data Q, R, S, P, T, U, V to identify the group Q, R, S (first input data) and to recognize the point P on the intracavitary ECG strip 8.

The second processing means 14, in this first embodiment, are associated with the additional unit 19 and with the second processing unit 13 for the acquisition and the processing of the second input data P and of the second recognition data J to obtain the aforementioned usage information H.

In this first embodiment, the processed usage information is the heights of the point P assessed with respect to the isoelectric line K and indicated by the letter H.

The usage information H, therefore, is at least in part of the type of heights of the point P assessed with respect to the isoelectric line K.

With the advancement of the catheter element 5, and therefore with the variation of the intracavitary ECG strip 8, the height of point P increases or decreases according to the position of the auxiliary electrode 7.

This information enables the operator to seek in a simple way the position in which H is maximum, i.e., the position corresponding to the position of the cavoatrial junction, indicated by the reference number 20.

In a second embodiment, the additional unit 19 is absent and the second processing means 14 are associated with the first processing unit 12 to receive the first recognition data Q, R, S, P, T, V, W, V, W, and with the second processing unit 13 to receive the second recognition data J.

The second configuration is particularly useful in case of ECG strips of patients with fibrillation under way, which means the "standard" pattern of the strip itself is lost.

In this case, the first recognition data processed are the points V and W, and the second recognition data J make reference to a condition in which it is hard to plot the isoelectric K.

In this second embodiment, the processed usage information H will be of the type of maximum heights evaluated between the absolute maximum point V and the minimum absolute point W of an intracavitary ECG strip 8 for a given cardiac cycle.

In this case too, the heights H will have a maximum value when the auxiliary electrode 7 finds itself at the cavoatrial junction 20.

The operation of an embodiment of the present invention is the following.

The electrodes 3 are arranged on the human body 4 in the positions usually adopted to operate the ECG device 2, permitting the detection of the surface ECG strips.

A medical operator starts the procedure for implanting the catheter element 5 by inserting this into a vein of the human body 4.

The auxiliary electrode 7 is connected to the ECG device 2 and so the intracavitary ECG strip 8 can be obtained.

The medical operator pushes the distal ending part 6 along the vein of the human body 4 which leads to the cavoatrial junction 20, proceeding with successive forward movements on pre-established positions.

For each position, the ECG device 2 provides the electronic device 9 with a surface ECG strip and an intracavitary ECG strip 8, both of which can be displayed on a specific monitor connected to the output unit 16.

In each position, furthermore, the module 10 detects and acquires the signal of the intracavitary ECG strip 8 to be processed.

In particular, the first processing means 11 process the signal of the ECG strip to obtain the recognition data Q, R, S, P, T, V, W, J.

The first data processing unit 12 finds the maximum and minimum points, processing the signal of the ECG strip and providing the first recognition data Q, R, S, P, T, V, W at output.

The second data processing unit 13 finds the points of equal potential and provides second recognition data J for the definition of the isoelectric line K on the ECG strip.

The recognition data Q, R, S, P, T, V, W, J are sent to the second processing means 14 which process them so as to obtain the usage information H.

The usage information H is in turn sent to the output unit 16 and therefore the medical operator manages to display them for each detection operation.

In particular, the usage information H has the character of measurement, and derives from the average of three detection operations.

By moving the distal ending part 6 gradually towards the cavoatrial junction 20, the usage information H changes, providing the medical surgeon with a reliable support, of a numerical character, on the positioning of the catheter element 5. The processing operations described above are reiterated for every different position until the information H is congruent with the correct position of the catheter element 5, i.e., at the cavoatrial junction 20.

For example, in the case of the information H being a height proportionate to the vector of the electrical activity of the heart, the information will be congruent when the height is maximum.

The memory unit 15 receives the data both from the ECG device 2 and from the module 10, allowing the recording of the usage information H and of the processed data in general, as well as of the ECG strips sent by the ECG device 2.

This way all the operations performed during implanting and related data can be filed and recorded.

The memory unit 15 also receives the data entered manually by the user interface module 17, thus enabling the medical operator to manage a greater amount of information, including during phases following the operation.

The ultrasound device 18 provides ultrasound data translatable into images to the memory unit 15 and to the output unit 16.

This way, the medical operator can have at disposal further information, e.g., on the diameters of the vein and the relative position for a correct introduction of the catheter element 5.

In the first embodiment (figures from 2 to 6), the first data processing unit 12 comprises an additional unit 19 wherein the first recognition data Q, R, S, P, T, V, W are further processed to provide further information.

In particular, the additional unit 19 identifies the first input data Q, R, S, corresponding to the group Q, R, S on the ECG strip and, starting with this, backs up along the ECG strip until it finds point P. The latter is provided at output as second input data P.

Figure 5:
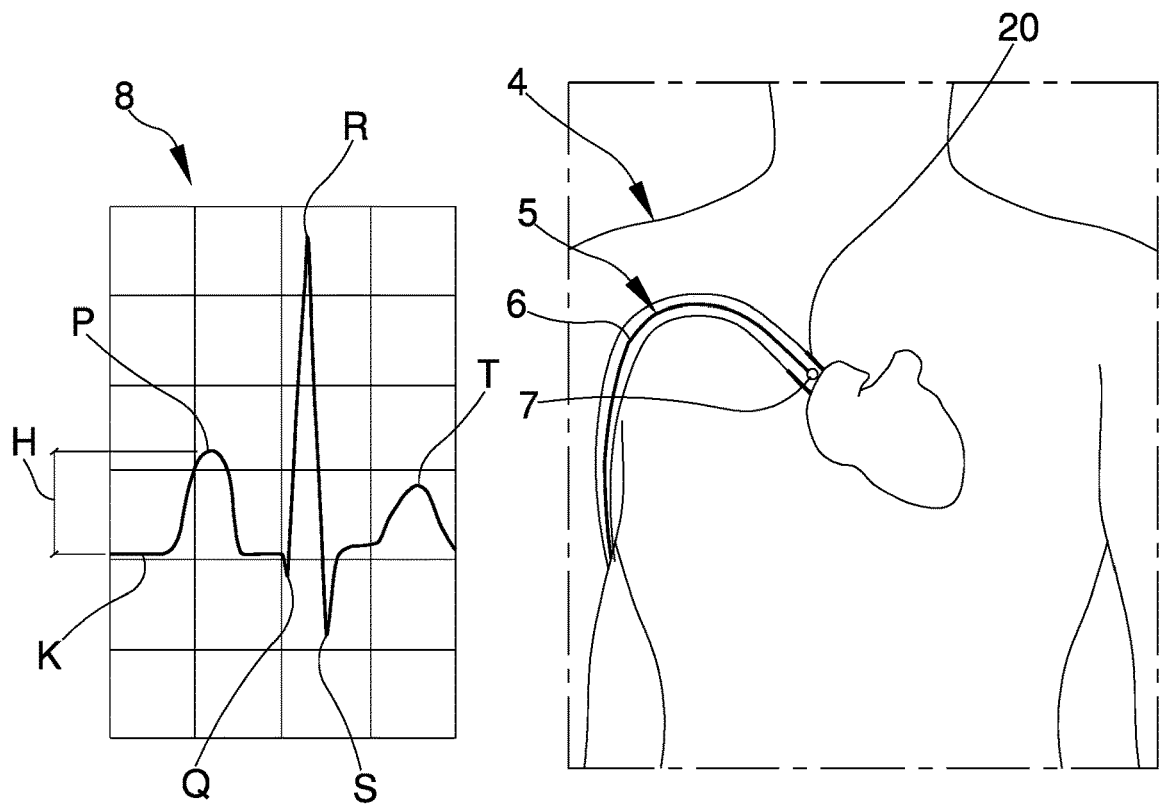

The second processing means 14 process the second output data P and the second recognition data J so as to obtain as usage information H the value of the heights of the point P on the ECG strip with respect to the isoelectric line K. As it gradually moves forward towards the cavoatrial junction 20, the value of the height H grows until it reaches its maximum precisely at the junction 20 (FIG. 5).

The medical staff can display this information and thus understand the positioning of the distal ending part 6.

Figure 6:
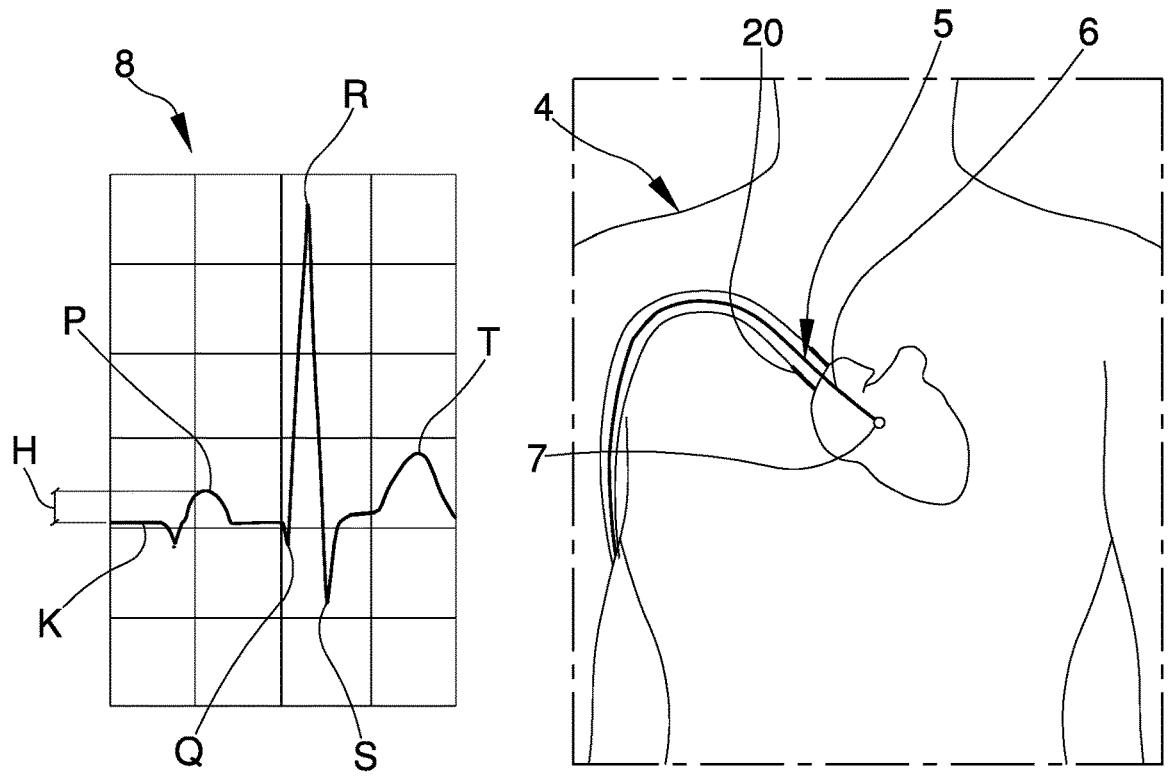
Figure 7:
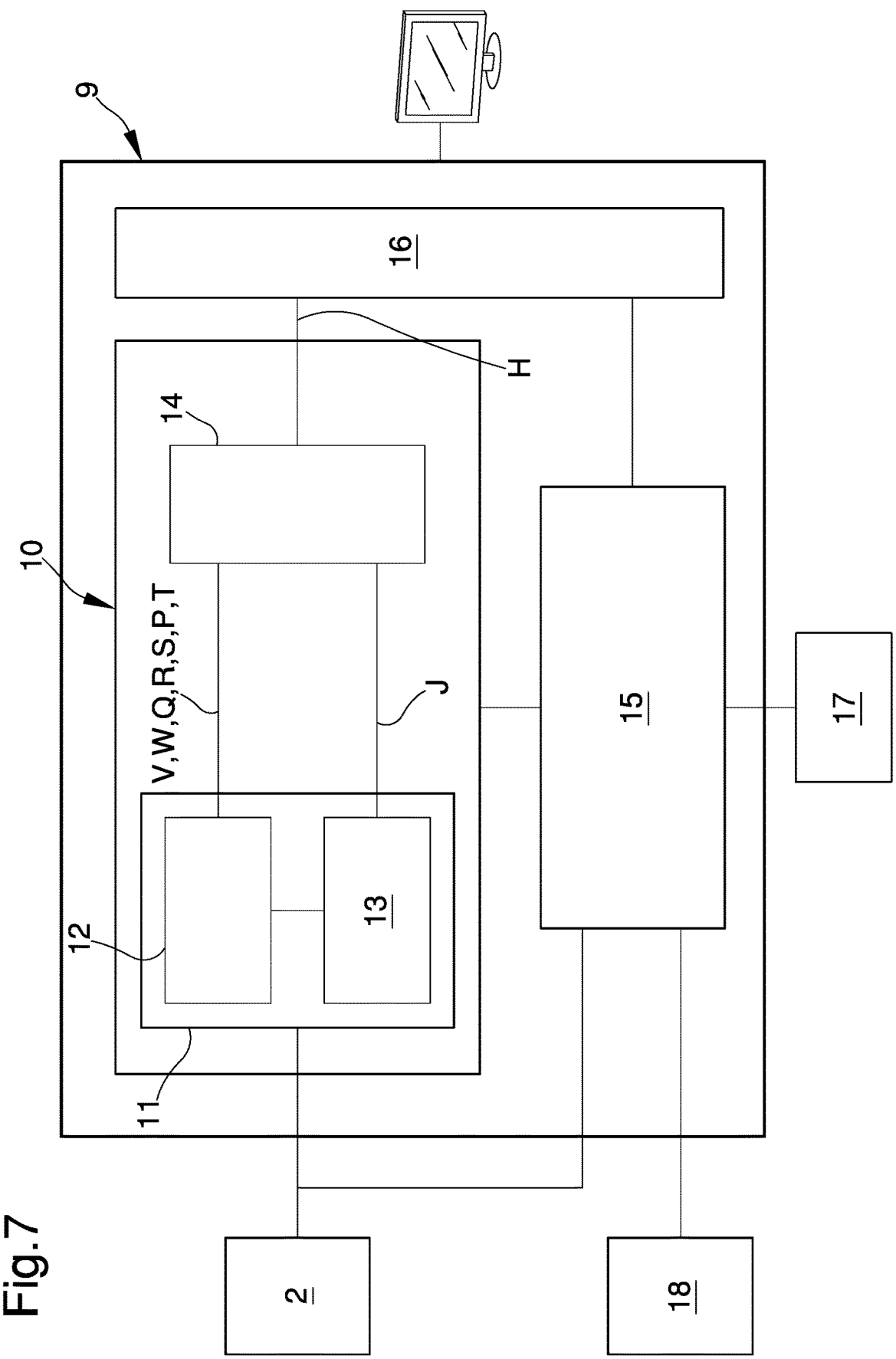
FIG. 7 is a schematic view of a detail of a second embodiment of the medical apparatus according to an embodiment of the invention.

In moving forward inside the heart (FIG. 6), in fact, the value of the height H starts to drop again, with the ECG strip which could appear to be "biphase" at the point P, i.e., a section with negative gradient (FIG. 6).

At this point, the doctor returns to the position whereby H appears maximum and can terminate the implant operations.

In a second embodiment, shown in the figures from 7 to 9, the first processing unit 12 sends the first recognition data Q, R, S, P, T, V, W directly to the second processing means 14, without identifying the point P.

Such embodiment is particularly suitable for those cases in which the patient is in a state of fibrillation, and consequently the ECG strip is not regular and it is not possible to identify the group Q, R, S and the point P.

In this case, the second processing means 14 receive the data referring to the values of the maximums and minimums of the ECG strip, in particular of the absolute maximum V and of the absolute minimum W and combine them with the second recognition data J.

The latter provide information useful for plotting lines with equal potential passing through the points V and W.

On the basis of these data and this information, the second processing means 14 provide usage information H at output which corresponds to the height measurable between the point V and the point W.

The usage information H, therefore, is at least in part of the type of heights measurable between the point V and the point W.

Similarly to what has been described for the first embodiment, in this case too, with the forward movement of the catheter element towards the junction 20 there is an increase in the height H which reaches its maximum value at the junction itself.

It has in practice been ascertained that the described embodiment of the invention achieves the intended objects and in particular the fact is underlined that the medical apparatus for the introduction of catheters into the human body permits improving the operations required for the implant of catheters.

The medical operator, in fact, can count on effective support whose information is reliable and sustained by the fact that it is obtained from an ECG strip with high resolution, higher than the resolution achievable using the naked eye from printed strips.

Furthermore, such apparatus allows minimizing the errors due to the doctor's assessments based on observations of the intracavitary ECG strip.

The information H, in fact, derives from the average of the three detected values, and consequently these can be considered real and true measurements. Consequently, the conditions of safety and health of the patients undergoing implants of central venous catheters appear improved.

Finally, the medical apparatus for the introduction of catheters into the human body allows providing information on the operating conditions of the already-implanted central venous catheters.

The operations described above, in fact, can also be easily performed for already-implanted catheters.

In this case it would be possible to monitor the position of the implanted catheter without maneuvering the catheter itself, thus enabling the doctor to make assessments as to the state of the implant before actually intervening.

This involves benefits both in terms of procedures, inasmuch as the number of operations can be reduced in the case of the control being successful, and in terms of the patient's health and safety, considering that there will be less risk of infections caused by maneuvers or repositioning jobs of the catheter.

Preferably, the data processing module 10 is a computer comprising at least a processor and a memory, the memory containing software modules able to be executed by the processor. In a variant, the data processing module 10 is a FPGA (Field Programmable Gate Array), or a ASIC (Applications Specific Integrated Circuit).

The first data processing means 11 and the second processing means 14 are preferentially formed as processor(s) of the computer.

As described above, for patients without fibrillation, the successive intracavitary ECG strips signals obtained from the auxiliary electrode element 7 at each position of the catheter 5 in the human body are acquired by the first data processing means 11.

For each ECG strip, the first data processing unit 12 of the first processing means 11 analyses the signal of the ECG trace to determine the successive local minima and maxima of the ECG strip which correspond to waves of the ECG strip.

The first data processing unit 12 in particular determines successive changes of the sign of slope of the signal.

Among the waves of the ECG strip, the additional unit 19 first identifies the Q, R, S group as a first input data, by determining three successive changes of the sign of the slope in the signal.

Then, as described above, the additional unit 19 simply identifies the presence of a P wave as a second input data, by backing in time along the ECG strip signal and by determining the onset of a peak, for example using a predetermined threshold.

Once the P wave has been determined, the second data processing unit 13 again backs in time from the P wave and finds an isoelectric line K by determining if at least three successive points, preferentially more than 4 successive points in the signal of the ECG strip are aligned.

The isoelectric line K forms second recognition data which serve as a baseline for determining the height of the P wave. Hence, the second processing means 14 use the second input data of the P wave and the second recognition data of the isoelectric line K to calculate a height H of the P wave in reference to the isoelectric line K.

The height H is determined for several successive ECG traces at the same position of the catheter 5 (for example at least 3, preferentially at least 10, more preferentially at least 20). The average height for several successive ECG traces at the same position of the catheter 5, forms usage information.

As described above, the usage information is advantageously displayed on a screen of the output unit 16. The medical operator is able to adjust the position of the catheter 5 in the human body based on the displayed value of the usage information, as described above.

In particular, the medical operator is able to identify the position at which the value of the height H is maximal, to define a reference position of the catheter distal ending part 6. The medical operator may thereafter adjust the position of the catheter ending part 6 by displacing the catheter 5 by a predetermined distance from the reference position, for example one or more centimeters from the reference position in either direction.

The usage information is obtained very simply, without requiring a time analysis or recording of the measured signal, by a mere data acquisition, which greatly simplifies the software and hardware used to carry out the method For a patient being in a state of fibrillation, the ECG traces may have a quite erratic shape without determined P wave.

In some cases, the additional unit 19 is able to identify the Q, R, S group, as explained above, by determining successive local minima and maxima of the ECG strip and/or successive changes of the sign of slope of the signal.

The additional unit 19 is however unable to determine the position and/or height of a P wave, since there is no P wave in the signal. Moreover, the second data processing unit 13 is unable to determine an isoelectric line K.

In that case, in a first embodiment described above, the first data processing unit 12 determines, in each interval between two successive Q, R, S groups identified by the additional unit 19, a point V corresponding to a positive absolute maximum of the ECG trace, and a point W corresponding to a negative absolute minimum of the ECG trace.

The second processing means 14 then calculate the height H shown in FIGS. 8 and 9 between the point V and the point W.

The height H is determined for several successive ECG traces at the same position of the catheter 5 (for example at least 3, preferentially at least 10, more preferentially at least 20). The average height for the several successive ECG traces at the same position of the catheter 5 forms usage information.

As described above, the usage information is advantageously displayed on a screen of the output unit 16. The medical operator is able to adjust the position of the catheter 5 in the human body, based on the displayed value of the usage information, as described above.

For example, the height H increases with the forward movement of the catheter element towards the junction 20, and has a maximum value when the auxiliary electrode 7 finds itself at the cavoatrial junction 20.

In another embodiment applicable for a patient in a state of fibrillation, only the point V corresponding to an absolute maximum of the ECG trace in each interval between two successive Q, R, S groups is used. The height of point V is determined by the first data processing unit 12 in reference to a baseline.

The baseline is advantageously chosen as a virtual reference line between the waves of the signal in each interval between two successive Q, R, S groups.

The virtual reference line is for example placed at a particular Y coordinate between the maximum value and the minimum value of the signal in each interval between two successive Q, R, S groups.

The second processing means 14 then calculate the positive height between the point V and the baseline. The height H is determined for several successive ECG traces at the same position of the catheter 5 (for example at least 3, preferentially at least 10, more preferentially at least 20). The average height for the several successive ECG traces at the same position of the catheter 5 (highest positive halfwave height), forms usage information.

In another embodiment applicable for a patient in a state of fibrillation, only the point W corresponding to an absolute minimum of the ECG trace in each interval between two successive Q, R, S groups is used. The height of point W is determined by the first data processing unit 12 in reference to a baseline.

The baseline is advantageously chosen as a virtual reference line between the waves of the signal in each interval between two successive Q, R, S groups.

The second processing means 14 then calculate the negative height between the point W and the baseline.

The height H is determined for several successive ECG traces at the same position of the catheter 5 (for example at least 3, preferentially at least 10, more preferentially at least 20). The average height for several successive ECG traces at the same position of the catheter 5 (highest negative halfwave height), forms usage information.

In again another embodiment applicable for a patient in a state of fibrillation, the first data processing unit 12 determines, in each interval between two successive Q, R, S groups identified by the additional unit 19, all the relative maxima F of the ECG trace, and advantageously, all the relative minima F' of the ECG trace.

The second processing means 14 then calculate the positive heights between each relative maximum F, each corresponding to a halfwave, and a baseline.

The baseline is advantageously chosen as a virtual reference line between the waves of the signal in each interval between two successive Q, R, S groups.

Advantageously, the second processing means 14 also calculate the negative heights between each relative minimum F', each corresponding to a halfwave, and the baseline The second processing means 14 then calculate an average of wave heights above the base line of the ECG trace in each interval between two successive Q, R, S groups.

The average of wave height above the baseline is averaged by the second processing means 14 over several successive ECG traces at the same position of the catheter 5 (for example at least 3, preferentially at least 10, more preferentially at least 20) to form usage information.

Advantageously, the average of wave heights below the baseline averaged by the second processing means 14 over several successive ECG at the same position of the catheter 5 also forms usage information.

What is claimed is:

1. A medical apparatus for the introduction of catheters into a human body, comprising:
    an ECG device having at least three electrodes, the at least three electrodes being positionable on the human body for the detection of surface electrical potential data and configured to output at least one surface ECG strip;
    at least one catheter element having a distal ending part, the distal ending part being positionable inside the human body and having an auxiliary electrode element for the detection of intracavitary electrical potential data associated with the ECG device, the auxiliary electrode element being configured for sending the intracavitary electrical potential data to the ECG device, the ECG device being configured to output at least one intracavitary ECG strip; and
    an electronic device associated with the ECG device, the electronic device configured for receiving the at least one intracavitary ECG strip and comprising a data processor system configured to process the at least one intracavitary ECG strip to obtain usage information adapted at least to provide instructions on insertion of the at least one catheter element in the human body,
    wherein the data processor system comprises a first data processor associated with the ECG device for acquiring the at least one intracavitary ECG strip, the first data processor being configured to obtain recognition data providing analytical information on the at least one intracavitary ECG strip,
    wherein the first data processor comprises a first data processor unit receiving an input of the at least one intracavitary ECG strip, the first data processor unit being configured to obtain first recognition data of maximum and minimum points of a same ECG strip of the at least one intracavitary ECG strip, the maximum and/or minimum points corresponding to waves of the same ECG strip,
    wherein the first data processor comprises a second data processor unit receiving an input of at least the intracavitary ECG strip and the first recognition data, the second data processor unit being configured to obtain second recognition data of points of an isoelectric line of the same ECG strip,
    wherein the electronic device comprises at least one output unit associated at least with the data processor system and adapted to output at least the usage information, the output unit being connectable to a screen configured to display the usage information, and
    wherein
        the usage information is at least in part of the height of a P wave assessed with respect to the isoelectric line, or
        the first data processor unit is configured to determine a point V corresponding to an absolute maximum of an ECG trace, a point W corresponding to an absolute minimum of the ECG trace, and/or an average of wave heights of the ECG trace, the usage information being at least in part of:
            a height of the point V,
            a height of the point W,
            a height measurable between the point V and the point W, and/or
            an average of wave heights of the ECG trace.

2. The medical apparatus according to claim 1, wherein the first data processor comprises an additional processor unit for processing the first recognition data to obtain first input data identifying a Q, R, S group on an ECG trace and second input data identifying the P wave on the ECG trace.

3. The medical apparatus according to claim 2, wherein the additional processor unit is configured for processing the first recognition data to obtain the first input data identifying successive Q, R, S groups on successive ECG traces, the first data processor unit being configured to determine the point V corresponding to the absolute maximum of the ECG trace and/or the point W corresponding to the absolute minimum of the ECG trace, between the two successive Q, R, S groups identified by the additional processor unit.

4. The medical apparatus according to claim 2, wherein the additional processor unit is configured to identify the first input data, corresponding to the group Q, R, S on the ECG strip and, starting from the group Q, R, S, and is configured to back up along the ECG strip until the additional processor unit finds the P wave which is provided as the second input data.

5. The medical apparatus according to claim 2, wherein the data processor system comprises a second data processor associated at least with the first data processor for acquiring and processing at least the first recognition data, the second data processor being configured to obtain the usage information.

6. The medical apparatus according to claim 5, wherein the second processor is associated with the additional processor unit and with the second data processor unit for the acquiring and the processing of the second input data identifying the P wave on the ECG trace and the second recognition data of points of the isoelectric line of the same ECG strip to obtain the usage information.

7. The medical apparatus according to claim 1, wherein the usage information is at least in part of a peak height measured on the at least one ECG strip.

8. A method of introducing at least one catheter into a human body, comprising:
positioning at least three electrodes of an ECG device of a medical apparatus on the human body for detecting surface electrical potential data and providing an output of at least one surface ECG strip;
positioning a distal ending part of at least one catheter element of the medical apparatus inside the human body, the at least one catheter element having an auxiliary electrode element for detecting intracavitary electrical potential data, associated with the ECG device, and sending to the ECG device the intracavitary electrical potential data, the ECG device providing at output at least one intracavitary ECG strip; and
receiving with an electronic device associated with the ECG device at least the intracavitary ECG strip and processing with a data processor system of the electronic device at least the intracavitary ECG strip to obtain usage information configured to at least to provide instructions on insertion of the at least one catheter element in the human body,
wherein the data processor system comprises a first data processor associated with the ECG device for acquiring at least the intracavitary ECG strip, the first data processor comprising a first data processor unit,
the method further comprising receiving an input in the first data processor unit of the at least one intracavitary ECG strip and obtaining with the first data processor unit, first recognition data of maximum and minimum points of a same ECG strip of the at least one intracavitary ECG strip, the maximum and/or minimum points corresponding to waves of the same ECG strip, wherein the first data processor comprise an additional processor unit for processing the first recognition data,
the method further comprising obtaining, with the additional processor unit, first input data identifying a Q, R, S group on an ECG trace and second input data identifying a P wave on the ECG trace,
the first data processor comprising a second data processor unit receiving at input at least the intracavitary ECG strip and the first recognition data,
the method further comprising obtaining, with the second data processor unit, second recognition data of points of an isoelectric line of the same ECG strip,
the data processor system comprising a second data processor associated at least with the first data processor for the acquisition and processing of at least the first recognition data,
wherein the electronic device comprises at least one output unit associated at least with the data processor system and adapted to output at least the usage information, the output unit being connected to a screen, the screen displaying the usage information,
the method further comprising:
obtaining the usage information by associating the second data processor with the additional unit and with the second processor unit to process the second input data identifying a P wave on the ECG trace and the second recognition data of points of the isoelectric line of the same ECG strip, or
determining, with the first data processor unit, a point V corresponding to an absolute maximum of an ECG trace between two successive Q, R, S groups, a point W corresponding to an absolute minimum of the ECG trace between two successive Q, R, S groups and/or an average of wave heights of the ECG trace between two successive Q, R, S groups, the usage information being at least in part:
a height of the point V,
a height of the point W,
a height between the point V and the point W, and/or
an average of wave heights of the ECG trace.

9. The method according to claim 8, wherein the human body is of a patient in a state of fibrillation, a standard pattern of the ECG strip being lost.

10. A method of introducing a catheter in a patient in a state of fibrillation, comprising:
positioning a distal ending part of at least one catheter element inside the patient in a state of fibrillation, the at least one catheter element having an auxiliary electrode element for the detecting intracavitary electrical potential data, associated with an ECG device;
sending to the ECG device the intracavitary electrical potential data, the ECG device providing an output of at least one intracavitary ECG strip;
analyzing the at least one intracavitary ECG strip with a data processor system associated with the ECG device to determine a point V corresponding to an absolute maximum of an ECG trace between two successive Q, R, S groups, a point W corresponding to an absolute minimum of the ECG trace between two successive Q, R, S groups and/or an average of wave heights of the ECG trace between two successive Q, R, S groups;
calculating with the data processor system a height of the point V, a height of the point W, a height between the point V and the point W and/or an average of the wave heights of the ECG trace; and
adjusting a position of the distal ending part of the catheter based on the height of the point V, the height of the point W, the height between the point V and the point W and/or the average of the wave heights of the ECG trace calculated with the data processor system.

11. The method according to claim 10, further comprising displaying on an output unit a value representative of the height of the point V, the height of the point W, the height between the point V and the point W and/or the average of the wave heights of the ECG trace calculated with the data processor system.

* * * * *